US006899698B2

(12) United States Patent
Sams

(10) Patent No.: US 6,899,698 B2
(45) Date of Patent: May 31, 2005

(54) ONE-WAY CLUTCH MECHANISMS AND INJECTOR DEVICES

(76) Inventor: Bernard Sams, 22 Avondale Avenue, London (GB), N12 8EJ ( * ) Notice: Subject to any disclaimer, the term of this patent is extended or adjusted under 35 U.S.C. 154(b) by 155 days.

(21) Appl. No.: 10/239,068

(22) PCT Filed: Mar. 22, 2001

(86) PCT No.: PCT/GB01/01271

§ 371 (c)(1),
(2), (4) Date: Sep. 18, 2002

(87) PCT Pub. No.: WO01/72361

PCT Pub. Date: Oct. 4, 2001

(65) Prior Publication Data

US 2003/0050609 A1 Mar. 13, 2003

(30) Foreign Application Priority Data

Mar. 24, 2000 (GB) .............................................. 0007071

(51) Int. Cl.[7] .......................... A61M 5/00; A61M 5/315
(52) U.S. Cl. ....................................... 604/211; 604/224
(58) Field of Search .............................. 604/68, 71, 72, 604/110, 131, 134, 135, 136, 138, 156, 157, 181, 186, 187, 194, 195, 196, 197, 199, 200, 207, 208, 209, 210, 211, 212, 214, 223, 224, 232, 246, 264, 272, 133

(56) References Cited

U.S. PATENT DOCUMENTS 5,674,204 A * 10/1997 Chanoch ...................... 604/211
5,743,889 A * 4/1998 Sams .......................... 604/211

* cited by examiner

Primary Examiner—Nicholas D. Lucchesi
Assistant Examiner—Mark K. Han
(74) Attorney, Agent, or Firm—McGarry Bair PC

(57) ABSTRACT

An incrementing mechanism suitable for use in a medical injector device has a driving member rotatably and slidably mounted within a tubular body and arranged to advance an elongate element in one direction with respect to the tubular body. A one-way clutch includes a generally conical surface and a blocking clutch member engageable with the conical surface. Means are provided to disengage the clutch, including a pressure component arranged and biased to engage the clutch member. Rotation of the driving member with respect to the pressure component causes two sets of inter-engageable teeth to ride over each other, which successively lifts the pressure component to disengage the clutch member from the conical surface and then allows the pressure component to be biased to a position where the clutch member engages the conical surface.

22 Claims, 11 Drawing Sheets

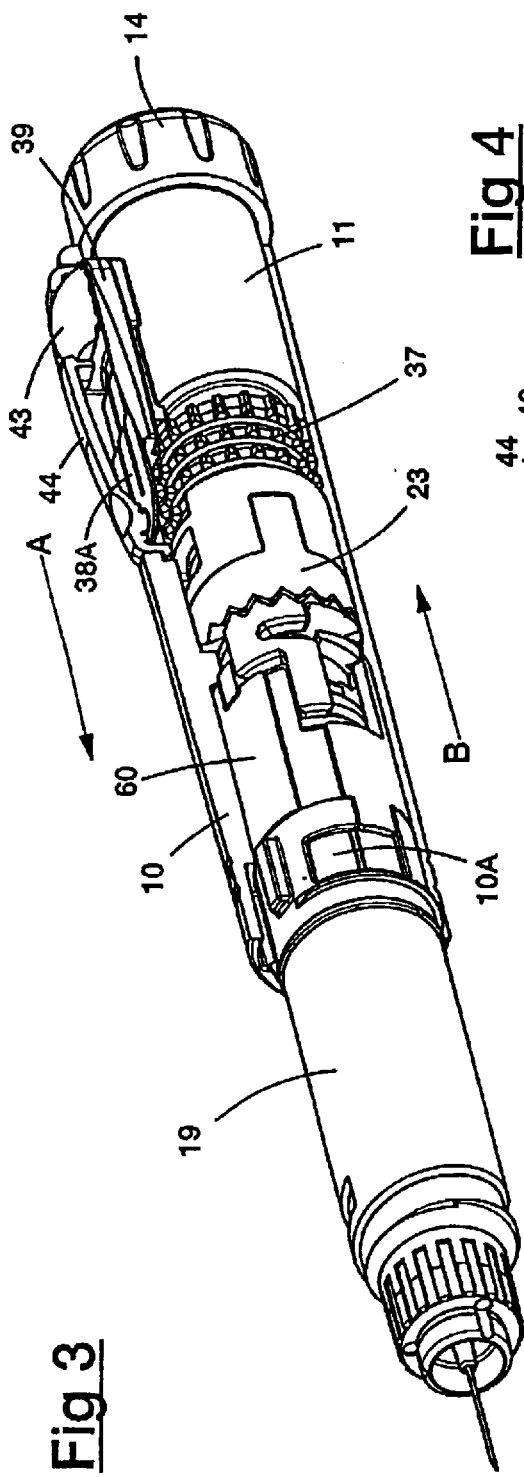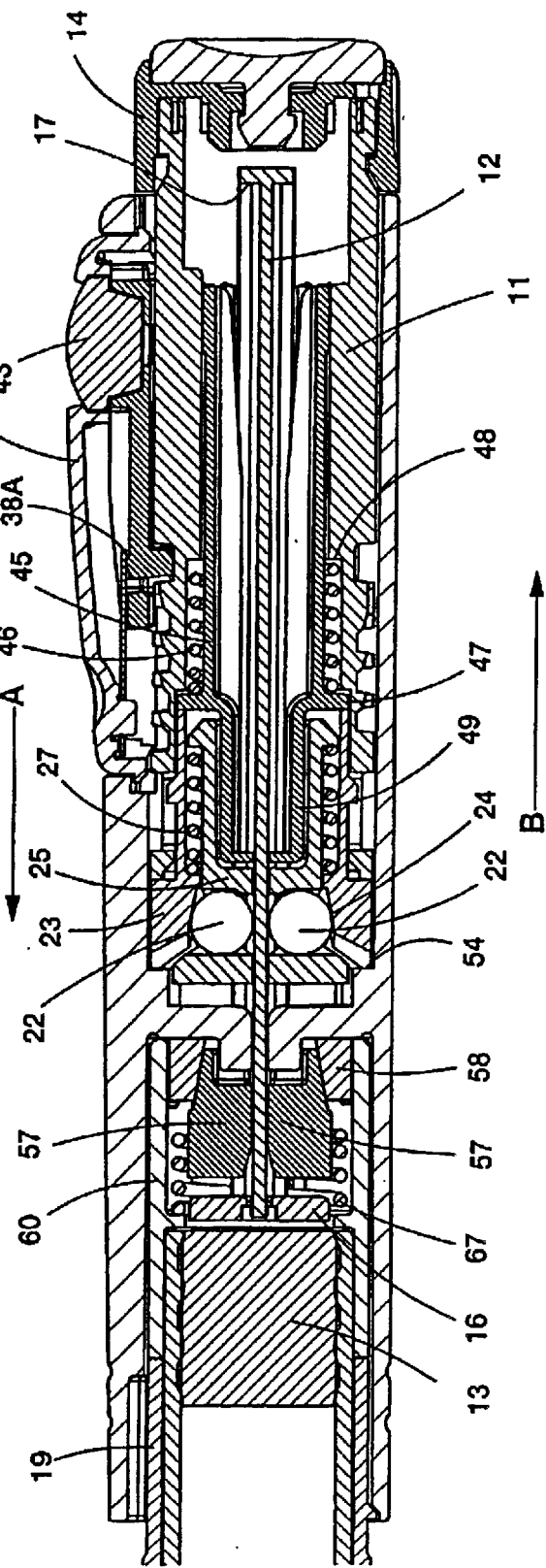

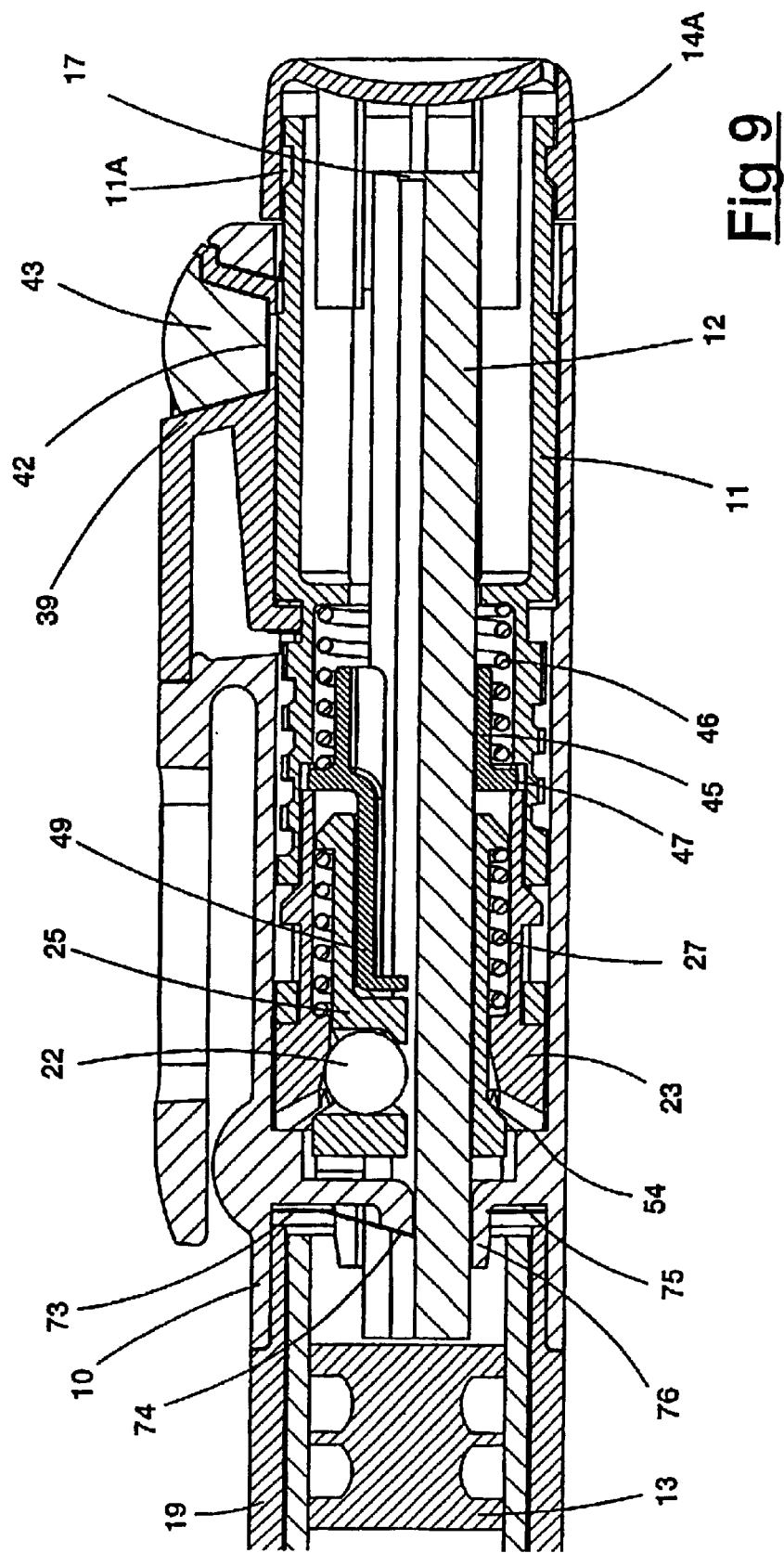

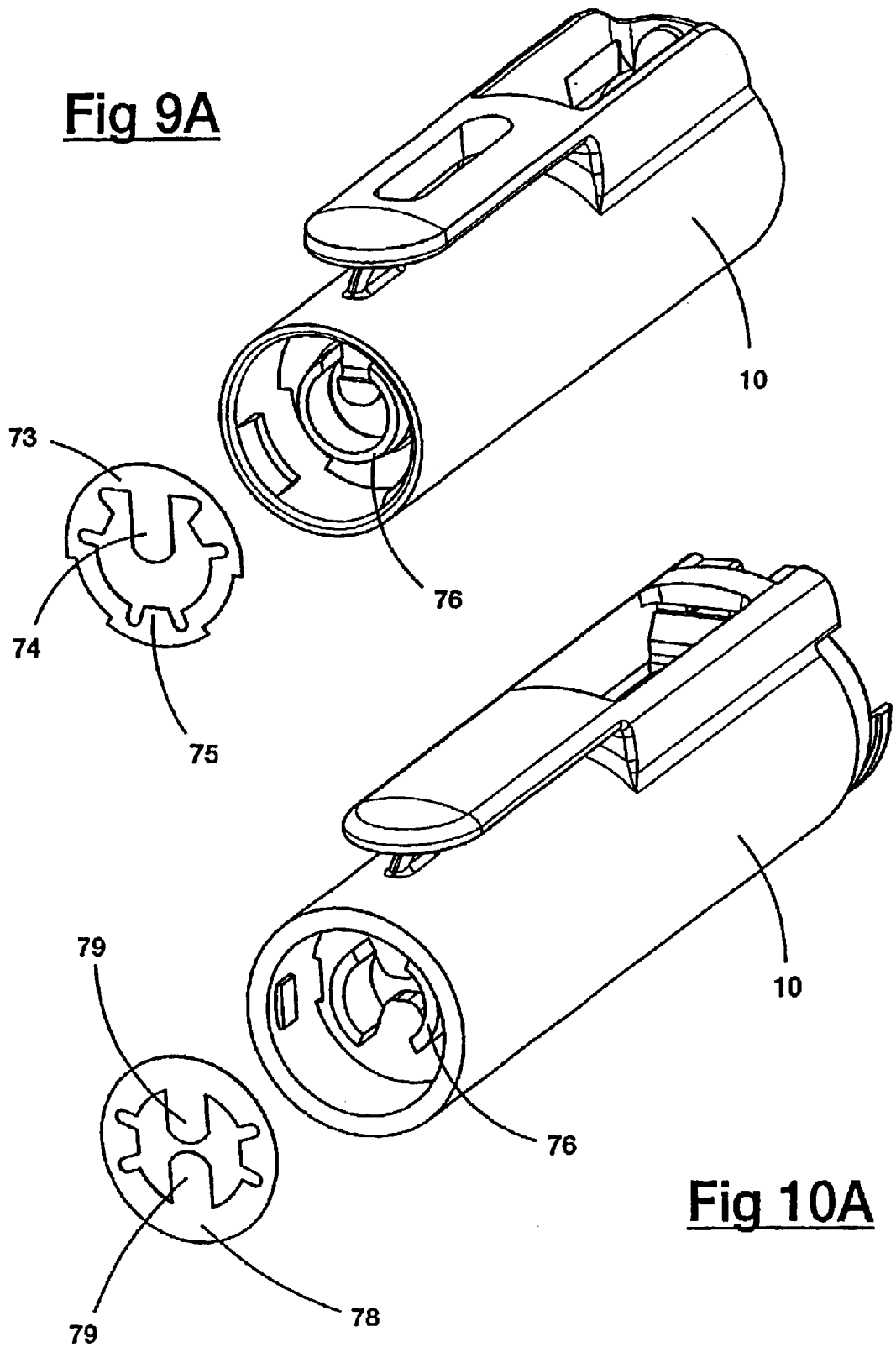

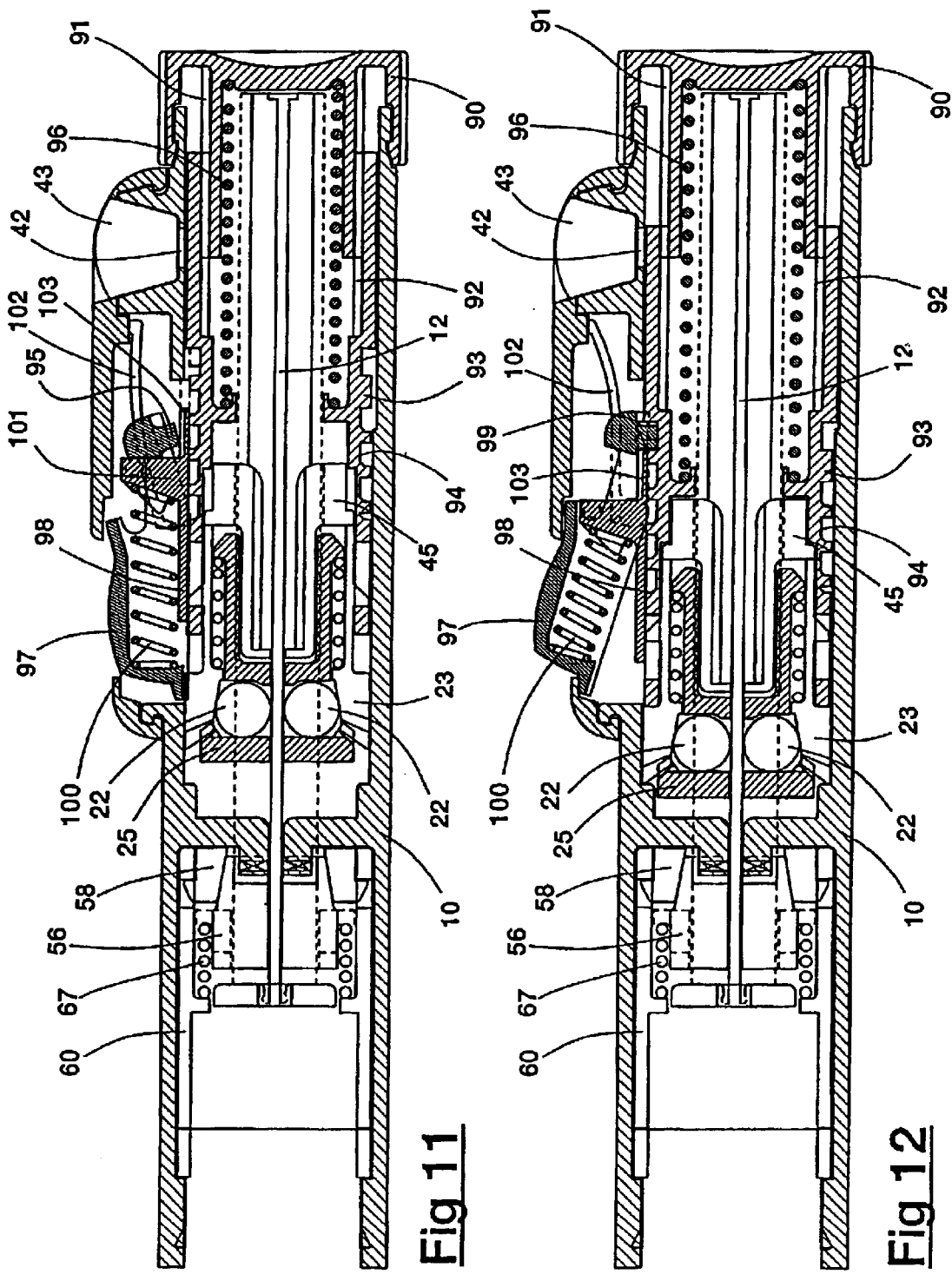

ONE-WAY CLUTCH MECHANISMS AND INJECTOR DEVICES

CROSS-REFERENCE TO RELATED APPLICATIONS

This application claims priority on International Application No. PCT/GBO1/01271, filed Mar. 22, 2001, which claims priority on British Application No. 00 07071.4, filed Mar. 24, 2000.

BACKGROUND OF THE INVENTION

1. Field of the invention

This invention relates to automatic one-way clutch means for use in an incrementing mechanism having a driving member rotatably and slidably mounted within a tubular body and arranged to advance an elongate element in one direction with respect to the tubular body within which the element also is mounted. In addition, in its preferred aspects this invention further relates to such an incrementing mechanism adapted for use in conjunction with an injector device to permit the accurate dispensing of a required pre-set dose of a medicament, whenever the device is used. The invention further relates to an injector device per se.

2. Related Art

In my EP-0673482-A, I have described and claimed an incrementing mechanism primarily intended for use with a hypodermic syringe, to permit the setting of a required dose of a medicament, such as insulin, whereafter the depression of plunger accurately dispenses the required dose through a needle connected to the syringe. The entire disclosure of the specification of EP-0673482 is incorporated herein by this reference thereto, and reference may be made thereto (or WO 94/15120, on which EP-0673482 is based) for a further description of the prior art mechanism.

Tests on and trials of the mechanisms described in EP-0673482 have lead to further development of those mechanisms to give improved operating performance, greater reliability and dose dispensing accuracy. It has also been possible to simplify the manufacture of the mechanisms and hence reduce the manufacturing costs, without compromising performance. Further development has resulted in three distinct versions of injector device incorporating the mechanisms—namely: (1) a disposable injector which is discarded when a cartridge containing the medicament has been exhausted; (2) a reusable injector which can be reset when a cartridge containing the medicament has been exhausted, so permitting the replacement of the spent cartridge by a new one; and (3) a repeatable pre-set dose injector which permits the initial setting of a required dose and thereafter can be used solely for the repeated dispensing of just that dose. All of these versions incorporate the improved automatic one-way clutch means of this invention, for the incrementing mechanism forming the basis of the injector.

SUMMARY OF THE INVENTION

According to its broadest aspect, this invention provides an automatic one-way clutch means for use in an incrementing mechanism having a driving member rotatably and slidably mounted within a tubular body and arranged to advance an elongate element in one direction with respect to the tubular body within which the elongate element also is mounted, which one-way clutch means comprises a channel extending along the element, a generally conical surface formed internally on the driving member and surrounding the element, a blocking clutch member located in the channel and engageable with the conical surface, and freeing means adapted to disengage the clutch by lifting the clutch member out of engagement with the conical surface so as to disconnect the driving member from said element, which freeing means comprises a pressure component held against rotation with respect to the element and arranged to engage the clutch member, a spring acting on said component to urge the component away from its clutch disengaging position, and two sets of interengageable teeth formed respectively around the driving member and around the pressure component whereby rotation of the driving member with respect to the pressure component successively lifts said component against the action of the spring to move the clutch member out of engagement with the conical surface and allows the spring to move the pressure component to a position where the clutch member engages said surface, through the interaction of the teeth riding over each other.

Though the one-way clutch mechanism of this invention could be used for purposes other than as a part of an injector device of the kind described hereinbefore, the primary intention is for the mechanism to be incorporated in such an injector. The invention will therefore be hereinafter described expressly with reference to that use, though it will be understood that the invention is not to be regarded as limited to that use.

The mechanism described in EP-0673482 has a one-way clutch including a generally conical surface 23 formed on a driving member (plunger 11), spring 25 bearing on a washer 24 to urge balls 22 into their active position. On rotating the driving member with respect to the elongate element (rod 12), internal walls 27 within the conical surface 23 serve to move the balls 22 away from their active positions, against the action of spring 25. This arrangement has the disadvantage that very tight tolerances are required during manufacture and also the number of times the clutch could be released on a full rotation of the driving member is severely limited. The consequence of this is that the read-out numerals for a set dose must be of a small height. A practical example of the earlier design allowed 4 released positions with a maximum of 12 on a full revolution of the driving member; and with each dose needing a forward movement of 0.138 mm of the elongate element (rod 12) the maximum numeral size was 1.656 mm.

In the mechanism of this invention, the generally conical surface may be substantially, or wholly, continuous, uninterrupted by the walls 27 of the previous design. This allows very many more clutch-released positions for each revolution of the driving member. A current preferred design has, in each set, teeth at 20° stations around the circumference and this results in a maximum numeral size of 2.484 mm. By positioning a lens over the window in the body through which the numerals are read, that may be increased to an effective height of over 4 mm.

It is highly preferred that the pressure component is additionally configured to urge the clutch member to its active, conical-surface engaging position. To this end, the teeth on the driving member and on the pressure component should be configured so that they do not fully interengage when meshed, so that the pressure component may still exert force on the clutch member. In turn this serves to ensure that there is a minimum of backlash between the driving member and the elongate rod, when the driving member is pressed in the one direction, which drives the elongate element to dispense a dose of medicament, when the mechanism is incorporated in an injector.

As with the previous design, it is preferred for there to be two diametrically opposed clutch members so as uniformly to distribute the forces, though it is possible a single clutch member could be employed. Each clutch member could be a wedge form integral with the pressure member, a floating wedge form or a conical roller, but preferably is a ball, located in a suitably shaped channel in the elongate element, so as to effect driving of that element upon depression of the driving member (the plunger, of the previous design).

In the previous design of injector, as described in EP-0673482, a helix (thread form) was formed in the internal surface of the tubular body and was engaged by a follower on the driving member such that rotation of the driving member threaded that member backwardly to pre-set a dose. Preferably, the design is reversed, so that the helix is now formed on the driving member, which carries the one-way clutch mechanism, and a follower is provided on the tubular body. In this case, the one-way clutch mechanism may be formed as a separate unit linked to the main part of the driving member by means of a lost motion mechanism, permitting a limited amount of axial movement between the two components but holding the two elements against relative rotational movement. This arrangement permits an annular groove to be formed at one end of the helix and in which the cam follower is disposed before the mechanism is set to dispense a dose. A spring loading applied to the driving member urges the follower to engage in the helix at the start of rotation of the driving member, to set the mechanism to its 'zero' position. The axial movement of the driving member to reach this position should be accommodated by the lost motion mechanism, with the mechanism then pulling the one-way clutch on further advancement of the driving member upon the rotation thereof.

Preferably, the mechanism includes means to prevent the selection of a dose for injection which is greater than the remaining dose in a cartridge of medicament coupled to the injector. Such means may include a coupler connected to the driving member and disposed about the elongate element, the coupler having projections which are engageable with an abutment at the end of the element. During the movement of the driving member away from its starting position by the rotation thereof, the coupler will move with that driving member but when the projection on the coupler engages the abutment on the end of the element, the coupler then prevents further axial movement of the driving member. In this way, once the maximum remaining dose in a cartridge has been selected, no greater dose may be set on the driving member, for dispensing.

An injector incorporating the mechanisms of the invention as described above may be arranged to allow the dispensing of a single cartridge of medicament, whereafter the entire injector is disposed of since the mechanism cannot be reset. In the alternative, the injector may permit the replacement of a spent cartridge by a fresh, fully charged cartridge, but in this case the mechanisms must permit the return of the elongate rod to its initial position, against the action of the one-way clutch mechanism and a further non-return clutch also incorporated in the injector as described in EP-0673482. Preferably, in the latter case, the disengagement of the cartridge from the main body of the injector automatically releases the further non-return clutch, so permitting the elongate element to be pushed back to its starting position, either manually or by the piston of a fresh cartridge, as the cartridge is offered to the injector and is secured thereto.

A modification of either form of the injector permits it to dispense repeated doses of up to a pre-set volume (number of units) less than the maximum volume which the injector is capable of dispensing. The pre-set maximum dose is selected by turning the driving member in the appropriate sense until a friction clutch starts slipping, whereafter the driving member is thrust forwardly to dispense the dose.

BRIEF DESCRIPTION OF THE DRAWINGS

By way of example only, several specific embodiments of injector incorporating an incrementing mechanism of this invention will now be described, reference being made to the accompanying drawings, in which:

FIGS. 1 to 7 show a first embodiment of injector;

FIGS. 8 and 9 show a second embodiment, in the form of a disposable mechanism;

FIGS. 11 and 12 show a third embodiment having a side button to release the mechanism.

Figure 1:
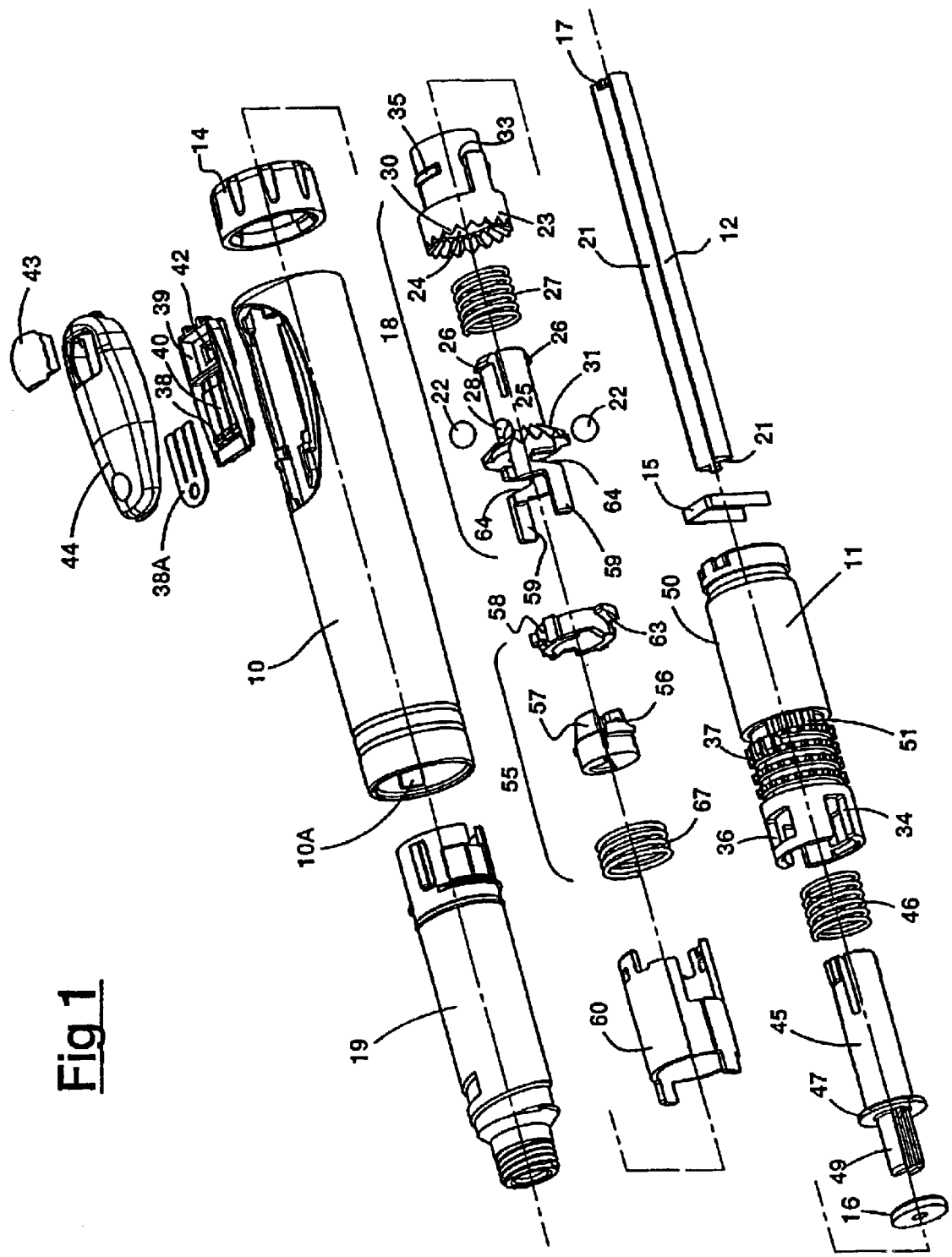
Figure 2A:
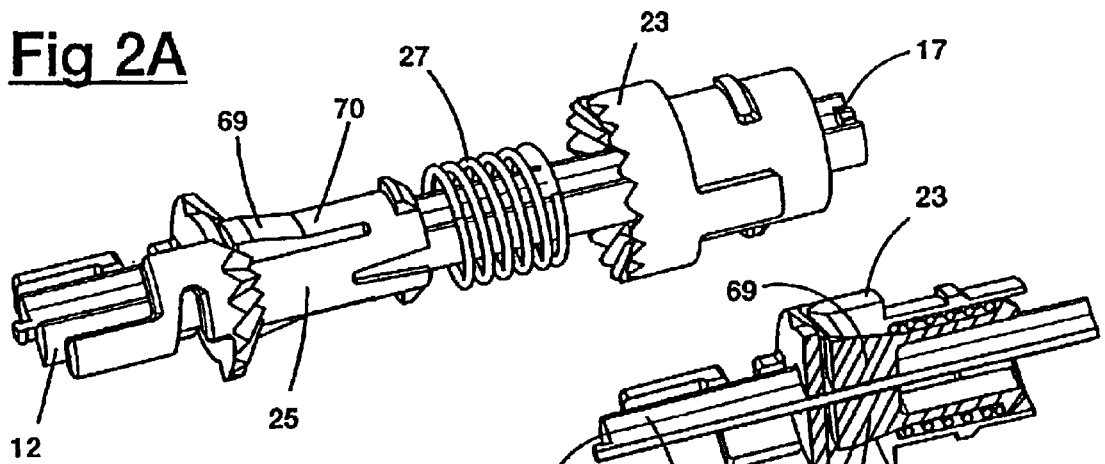
Figure 2B:
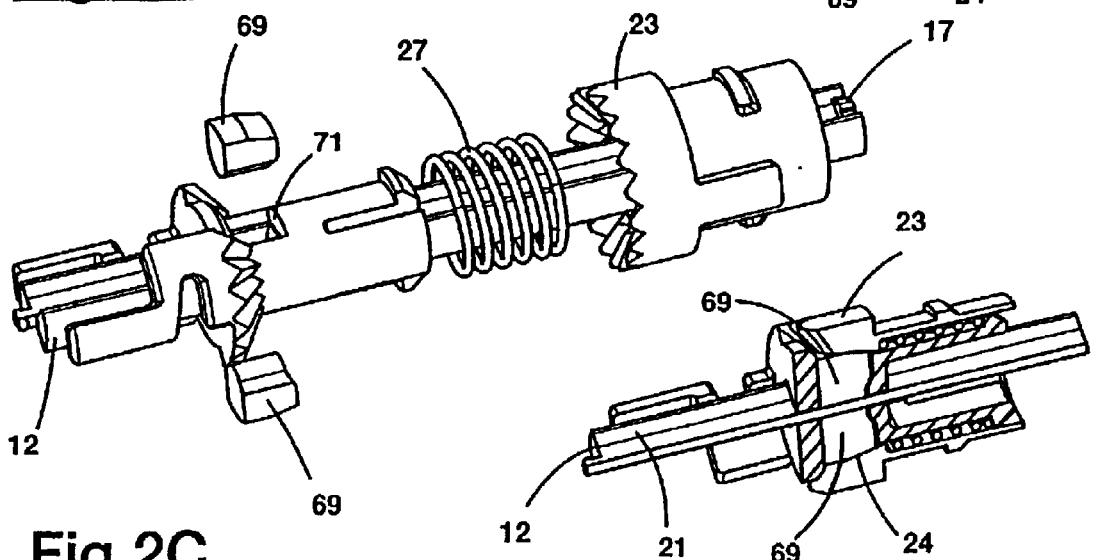
Figure 2C:
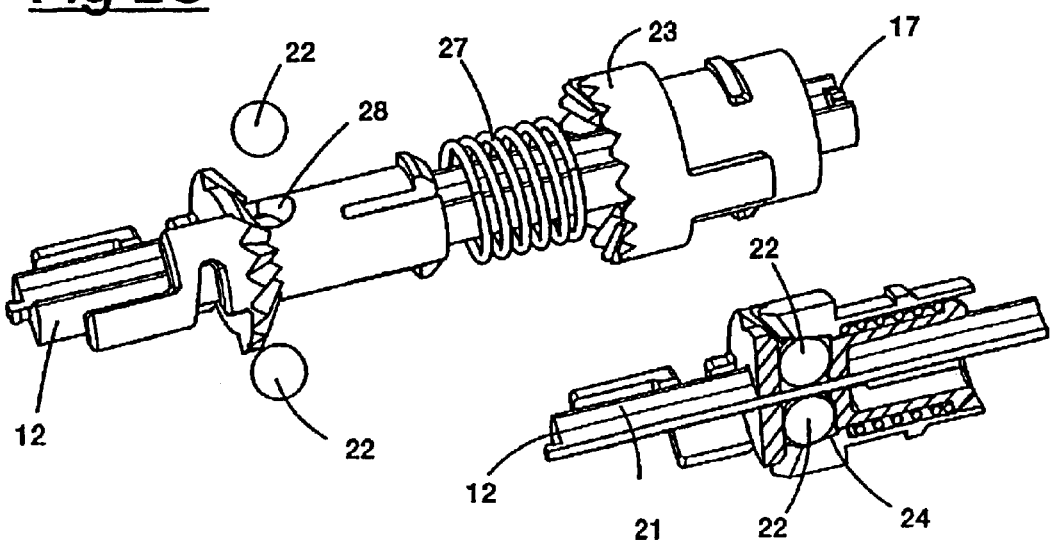
Figure 5A:
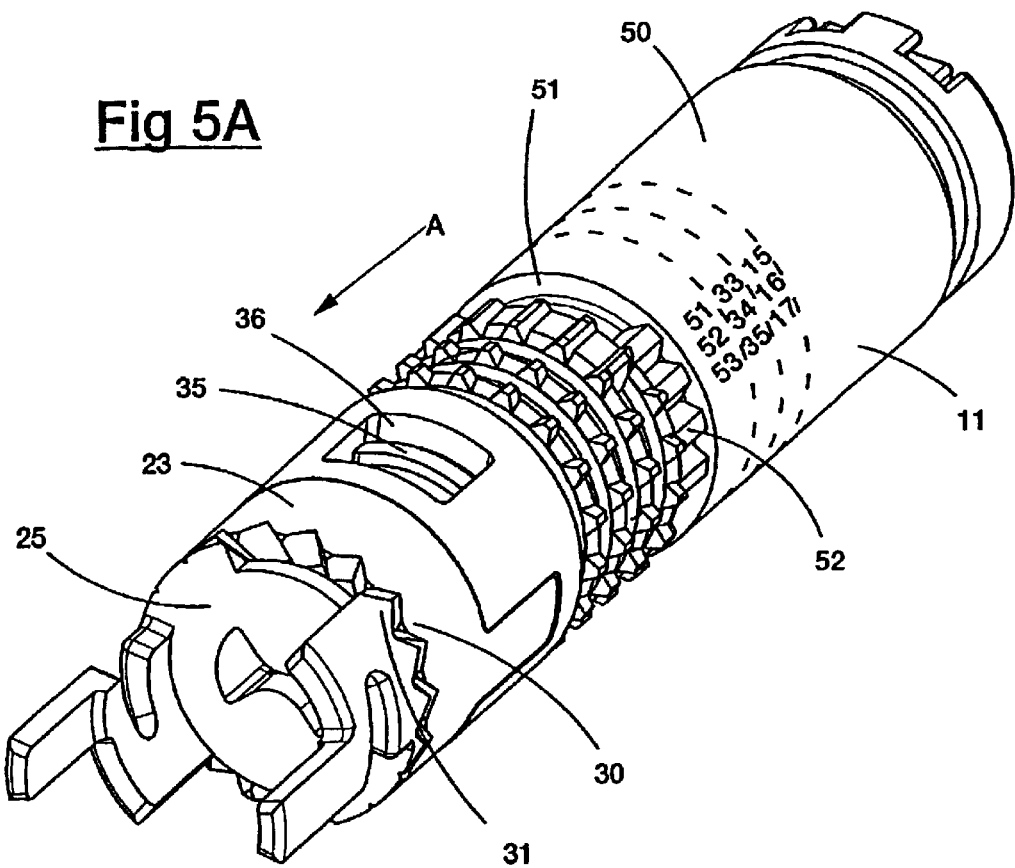
Figure 5B:
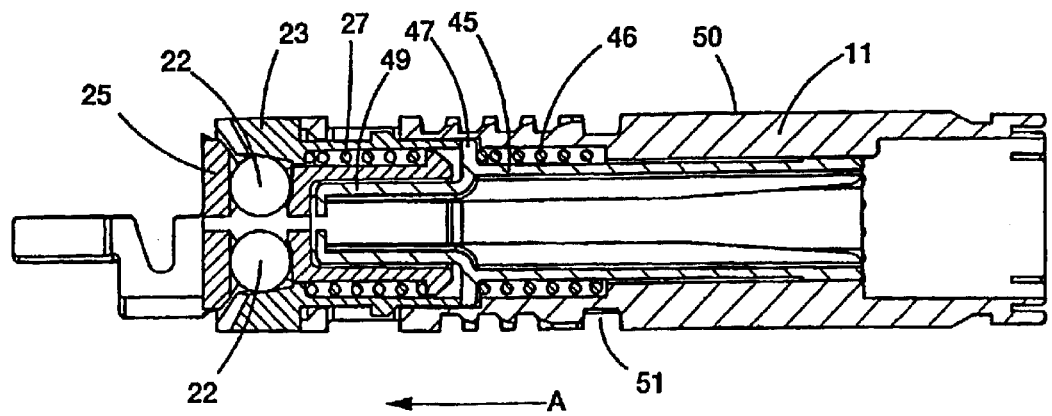
Figure 6:
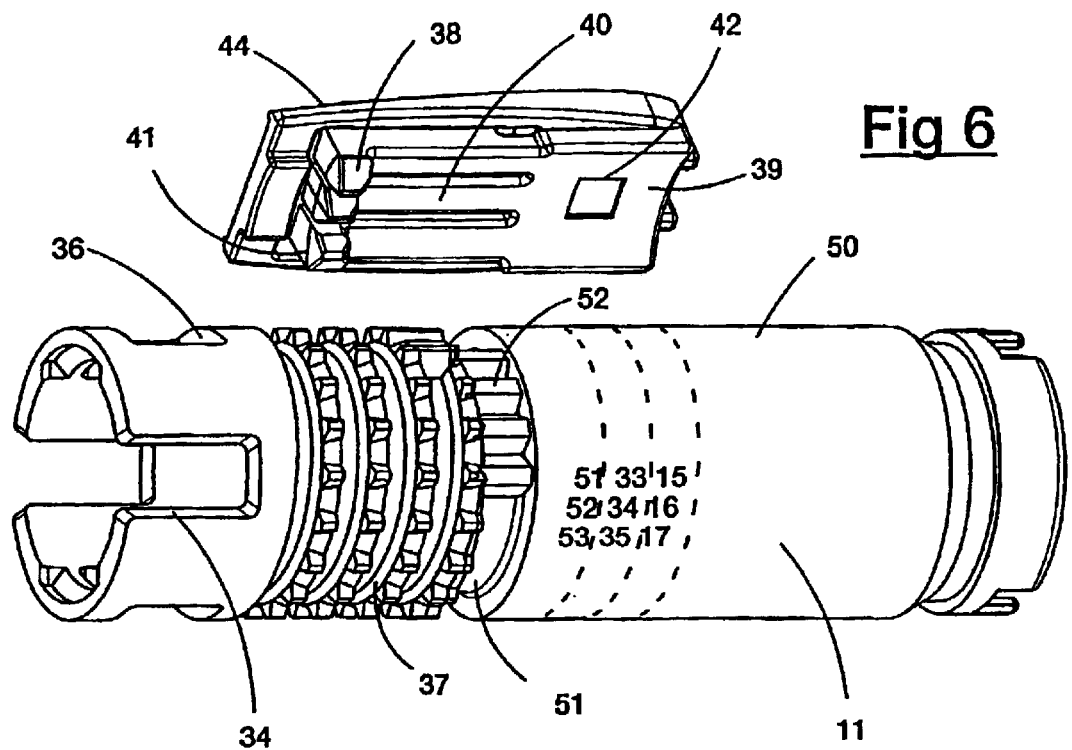
Figure 7:
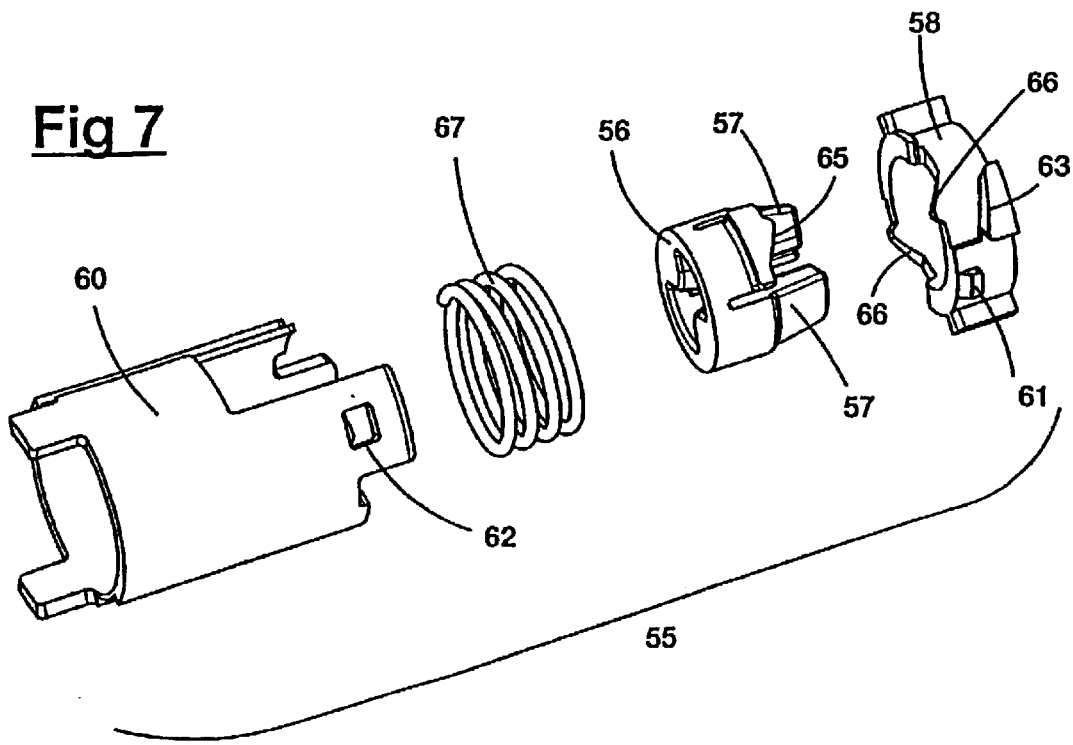
Figure 8:
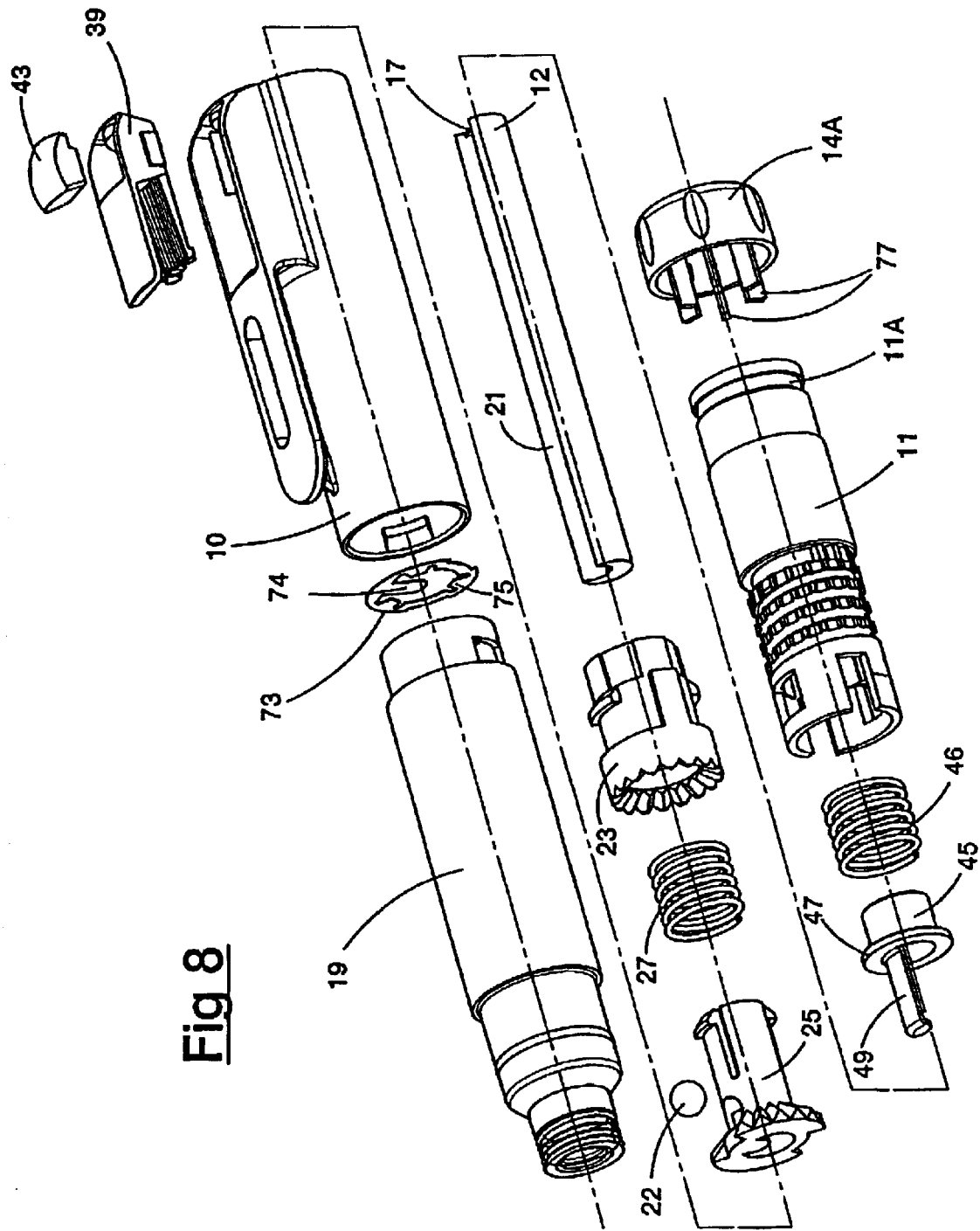
Figure 10:
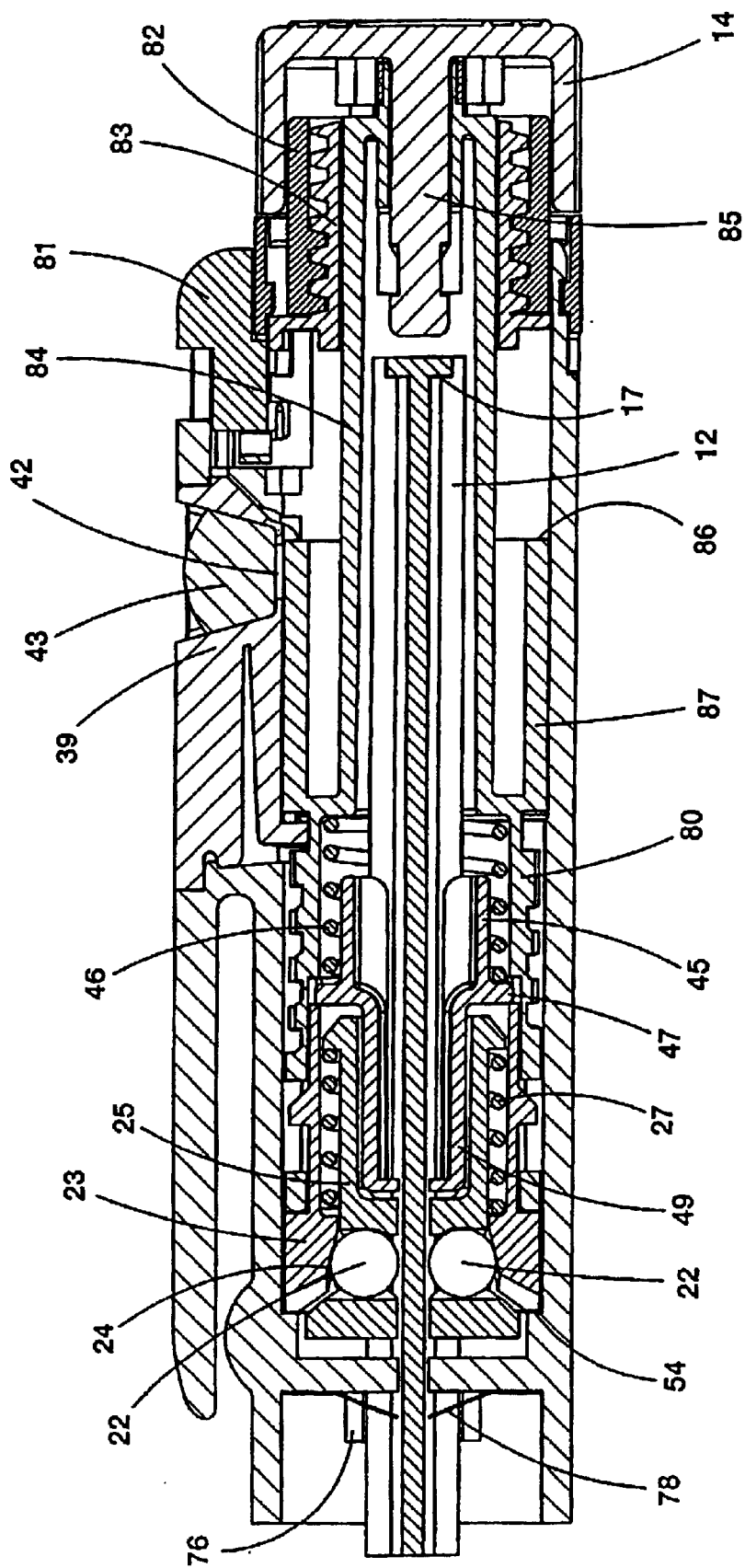
FIG. 10 shows a modified form of the second embodiment, again in the form of a disposable mechanism.
Figure 13A:
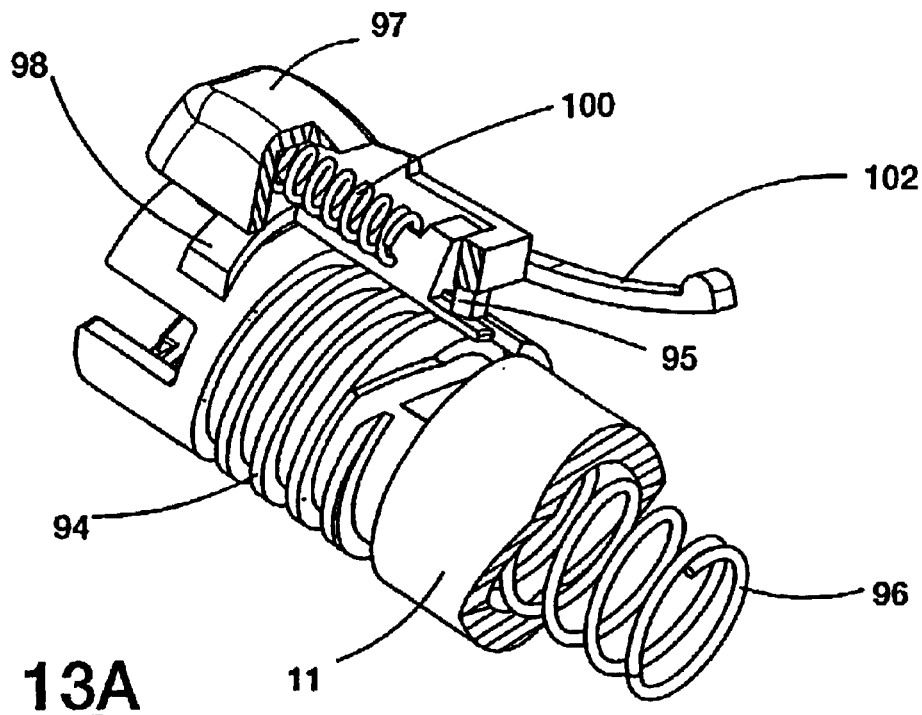
Figure 13B:
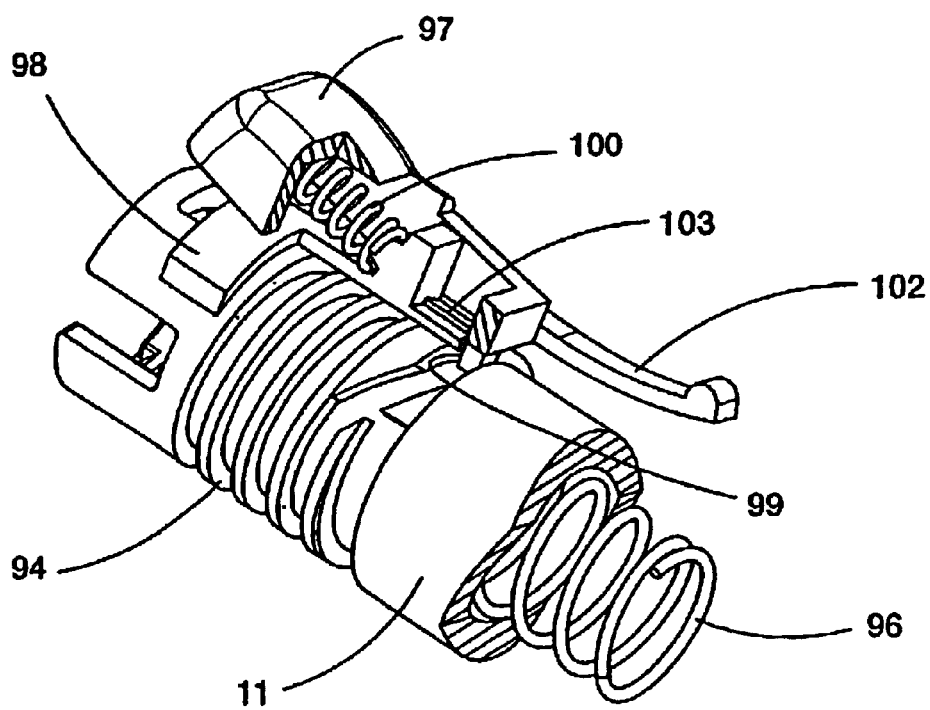

In more detail:

FIG. 1 is an exploded isometric view showing the individual components of the first embodiment;

FIGS. 2A, 2B and 2C respectively show three alternative clutch mechanisms, the mechanism of FIG. 2C being used in the embodiment shown in FIG. 1 and in each case, the Figure showing both an expanded isometric view and an assembled cut-away view;

FIG. 3 is a partially cut-away isometric view of the assembled injector of FIG. 1;

FIG. 4 is an axial section through the mechanism of FIGS. 1 and 3;

FIGS. 5A and 5B are respectively isometric and axial sections through the plunger and components associated therewith;

FIG. 6 shows in more detail the helix on the plunger and the followers which co-operate therewith;

FIG. 7 shows a further one-way clutch mechanism used in the injector of FIGS. 1 and 3;

FIG. 8 is an exploded isometric view showing the individual components of the second embodiment;

FIG. 9 is an axial section through the mechanism of FIG. 8;

FIG. 9A is an isometric end view on a part of the mechanism of FIG. 9;

FIG. 10 is an axial section through a modified form of the mechanism of FIG. 8;

FIG. 10A is an isometric end view on a part of the mechanism of FIG. 10;

FIGS. 11 and 12 are axial sections through a third embodiment, respectively when set to perform an injection and having performed an injection; and FIGS. 13A and 13B are detail partial views on the release mechanism of the third embodiment.

DETAILED DESCRIPTION OF THE INVENTION

In the following description, references to "forwardly" and "rearwardly" are intended to refer to the normal disposition of an injector and thus the forward end thereof is that carrying a needle which performs the injection and the rearward end is that which is depressed, to dispense a dose of medicament. In the Figures, the forward end is that shown on the left and the rearward end that shown on the right.

Referring initially to FIGS. 1 to 7, the injector comprises a tubular body 10 within which is mounted a plunger 11 and a co-axial elongate rod 12 for acting on the piston 13 (FIG. 4) of a cartridge of medicament, located within a cartridge holder 19, held to the body 10 by a bayonet connection.

The plunger 11 is generally tubular and has at its rear end an end-cap 14 connected to the plunger through a friction clutch including spring 15, which clutch slips in the event that a rotating force is applied to the end-cap 14 and which rotation cannot be transferred to the plunger for reasons to be described below. Slidably received within the plunger 11 is the rod 12, a washer 16 being mounted on its forward end to give a large area to contact piston 13. At the rearward end, the rod 12 has a stop 17, for a purpose to be described below.

At the forward end of the plunger 11, there is provided an automatic one-way clutch mechanism 18 shown in more detail in FIGS. 2, 4, and 5B and which serves to couple the plunger 11 to the rod 12 when the plunger is driven forwardly (to the left) in the direction of arrow A but allows the plunger 11 to be moved rearwardly in the direction of arrow B, whilst the rod 12 remains stationary.

The rod 12 has a generally H-shaped cross-section defining two channels 21 in each of which is located a respective ball 22. The clutch mechanism includes a cone member 23 defining an internal conical surface 24 overlying the balls 22, such that on forward movement of the cone member 23, the balls 22 are jammed in the space between the cone member and rod, so coupling the cone member to the rod. On rearward movement of the cone member, the balls may roll to a wider part of the space between the cone member and the rod, thus disconnecting the cone member and the rod.

A pressure component 25 is slidably arranged on the rod 12 and extends through the cone member 23, the pressure component having at its rearward end an opposed pair of upstanding ribs 26. A compression spring 27 acts between those ribs and a shoulder in the cone member, so thrusting the pressure component to the right with respect to the cone member (FIG. 4). The pressure component has a pair of opposed radial sockets 28 with the balls 22 located in those sockets; movement of the pressure component 25 to the left against the action of spring 27 thus frees the one-way clutch mechanism, whereas movement of the pressure component to the right under the action of the spring 27 urges the balls into the gap between the conical surface and the rod, so engaging the clutch mechanism 18.

Around the forward end of the cone member 23 are formed axially projecting teeth 30, the pressure component 25 having a flange on which are formed generally similar teeth 31 inter-engageable with the teeth 30. Rotation of the cone member 23 thus will cause the teeth respectively on the cone member and the pressure component to override one another, so alternately lifting the pressure component against the spring bias, and allowing the spring bias to jam the balls between the conical surface and the rod. The teeth are formed such that they do not fully inter-engage, so ensuring that the sockets 28 always apply a spring load on the balls, when the pressure component has not been lifted by the teeth.

The outer surface of the cone member 23 has a pair of opposed lugs 33 which are received in corresponding slots 34 in the plunger 11. The slots and lugs are configured so that there is essentially no rotational backlash between the two components though there is lost axial motion between the cone member and the plunger, controlled by catches 35 on the cone member and received in apertures 36 in the plunger.

Rearwardly of the clutch mechanism 18, the plunger 11 is formed with an external precision helix 37 (see particularly FIGS. 3 and 6), in effect having a toothed form and which is engaged by three cam followers 38 resiliently movable in the radial direction. The followers are formed as a separate component 39 secured to the tubular body 10; each follower is in the form of an arm 40 projecting from that component 39 and having at its forward end a chambered tooth 41 engageable in the helix. Further, the follower teeth 41 are arranged on the same helical pitch as the helix 37 on the plunger. The component 39 also defines a window 42 into which is fitted a magnifying lens 43, positioned within a cover 44. A spring-assister 38A is arranged between the cover 44 and the followers 38 to ensure adequate engagement with the helix 37.

A coupler 45 is located partially within the plunger 11 and is arranged to prevent setting of the injector to a dose greater than that remaining within a connected cartridge. Spring 46 acts between a flange 47 on the coupler 45 and an internal shoulder 48 of the plunger (FIG. 4) so as to urge the coupler forwardly, whilst simultaneously urging the plunger rearwardly. The flange 47 engages the rear face of the cone member 23, the coupler having a pair of arms 49 projecting forwardly within the pressure component 25 and having hook-shaped forward ends. These forward ends are engageable by the stop 17 on rod 12, so as to prevent further rearward movement of the plunger once so engaged. Further, the forward ends engaging the stop 17 prevent the rod 12 being pulled forwardly out of the assembly when no cartridge is present.

The plunger has a cylindrical external surface 50 between the helix 37 and its rearward end, on which surface are marked in a helical fashion numerical indicators of the dose to be dispensed following setting of the mechanism. The set dose is viewable through the lens 43 located in the window 42.

The rearward end of the helix 37 runs into an annular groove 51 in which the teeth 41 of the followers 38 are received when the injector is in its initial setting. Referring particularly to FIGS. 5A and 6, there are upstands 52 in the annular groove 51 aligned with valleys between the teeth of the helix 37, at the zero position of the plunger. On rotating the plunger 11 by means of the end-cap 14 in the correct sense (clockwise, when viewed from the rear end), the spring 46 urges the plunger 11 to the right so permitting the teeth 41 of the cam followers to engage into the helical thread when all three follower teeth are on their respective upstands 52 in the groove 51, this occurring at the zero position of the plunger. The chambers on the respective teeth facilitate the engagement of the follower teeth 41 into the helix 37.

Initially, with the teeth 41 in the annular groove, a colored band is visible through window 42 but when the followers engage the thread, at the zero position, the numeral '0' is visible through the window. Continued rotation of the end-cap 14 winds the plunger 11 further to the right, with the selected dose visible through the window incrementing as this continues. Once the set dose has been achieved, a connected needle 53 is inserted into a suitable site and the end-cap 14 depressed to effect dispensing of the selected dose. This is achieved by the plunger pushing the cone member 23 to the left, the one-way clutch mechanism 18 coupling the leftward movement of the cone member 23 to the rod 12, the forward end of which bears on the piston 13 of a connected cartridge of medicament, so moving the piston to dispense that medicament. Movement of the plunger 11 is continued until the outer edge of the cone member 23 engages an abutment 54 formed on an internal wall within the body 10 and through which the rod 12 passes in a slidable, but non-rotatable, manner.

During the driving of the plunger 11 to the left, the teeth 41 of the cam followers 38 ride over the parts of the helix having a relatively low angle; but when the plunger is set between doses, the plunger cannot be driven to the left by virtue of the profile of the helix. Moreover, the rear wall of the helix is relatively sharp, so that the followers prevent the plunger being pulled rearwardly.

As the dose is being set, the cone member 23 rotates with respect to the pressure component 25, so lifting that component each time the teeth ride over each other, as described above. This also has the action of freeing the clutch between the set doses and thus there is no penalty in over-shooting the required dose and then winding the end-cap 14 in the opposite sense, from a larger dose to a lesser dose, since this will not significantly drive the rod 12 forwardly.

During movement of the plunger 11 to the right, by rotation of the end-cap 14, the rod 12 is held against rearward movement by a further one-way clutch mechanism 55, provided forwardly of the internal wall defining abutment 54. This clutch mechanism 55 has a check member 56 with two integrally hinged wedges 57 located in the channels 21 of the rod 12 and around which is disposed a locking component 58 the internal profile of which drives the wedges 57 into engagement with the rod 12—see particularly FIG. 7. In the normal loaded position shown in FIG. 3, the wedges 57 serve as a one-way clutch to prevent rearward movement of the rod 12, whilst permitting free forward movement of that rod. The locking component 58 is coupled to the pressure component 25 by legs 59 projecting forwardly from that component through slots (not shown) formed in the internal wall in the tubular body 10. The locking component 58 is engaged with a tubular key 60 by means of clips 61 located in holes 62 in the key 60.

The key forms a part of a bayonet locking mechanism for the cartridge holder 19, as well as controlling action of the further clutch mechanism 55. The cartridge holder 19, containing a cartridge of medicament, is loaded by pushing the cartridge holder rearwardly with respect to the body 10 to engage the bayonet slots of the holder with lugs 10A formed internally within the forward end of the body 10. Twisting the holder to complete the bayonet connection turns the key 60, which rotates the locking component 58 to bring check member 56 into engagement with rod 12. This releases the pressure component 25 from being pulled forward, so that dose setting can subsequently be performed. Removal of the cartridge holder by releasing the bayonet connection re-sets the key 60 to pull forward the pressure component 25 and so free the check member 56; in turn this allows the rod 12 to be pushed rearwardly back to its initial position.

Cams 63, formed on the external surface of the locking component 58, prevent rotation of that component until aligned with the recesses 64, so that cartridge replacement cannot take place until the plunger 11 is in its forward position. Turning the key 60 on disconnecting the cartridge holder also pushes the check member 56 away from locking component 58 through further inter-engaging cam surfaces 65 and 66 against the action of internal spring 67, thereby releasing the wedges 57 from the locking component 58. Rod 12 can now be moved in either direction and may be pushed rearwardly, either manually or by the piston 13 of a fresh cartridge, ready to dispense a new dose.

The above described embodiment uses a one-way clutch mechanism 18 as shown in FIG. 2C. However, that mechanism could take other forms, such as shown in FIGS. 2A or 2B. In FIG. 2, like parts are given like reference numbers. In FIG. 2A, the pressure component has wedges 69 formed integrally therewith, on resilient arms 70. The profile of the channels 21 in rod 12 may need to be modified so as to suit these wedges. In the arrangement of FIG. 2B, the wedges 69 are formed separately and are received in apertures 71 in the pressure component. A further possibility would be to provide rollers of a somewhat conical form so as to give a three line contact. These arrangements may be more preferred than the use of balls, as shown in FIG. 2C, to avoid high point loadings on the conical surface 24 of the cone member 23 and on the rod 12, which could lead to dimpling of that surface 24 and rod 12.

The injector of FIGS. 8 and 9 differs from that of FIGS. 1 to 7 in that the one-way clutch mechanism 18 is simplified and uses only one ball, rather than the two balls of FIGS. 1 and 2C. The further one-way clutch mechanism 55 is omitted and is replaced by a simple locking washer 73 (see particularly FIG. 9A) to prevent rearward movement of the rod 12. Also, the end cap arrangement is modified in that spring 15 is omitted; rather an integral spring is formed with the modified end cap 14A. In other respects the injector corresponds to the first embodiment described above. Consequently, like parts are given like reference characters and will not be described again here.

The locking washer 73 is of pressed spring steel and has an inwardly projecting tooth 74 which locates in the channel 21 of the rod 12, forwardly of the internal wall of the tubular body 10. The washer also has two or more inwardly projecting arms 75 which are pushed into engagement with a raised boss 76 on the forward face of the internal wall, as shown in FIGS. 9 and 9A. As best seen in FIG. 9, the tooth 74 is deformed forwardly by the action of fitting the washer on the rod; any attempt to move the rod rearwardly is resisted by that tooth, digging into the material of the rod. As described above, a dose is dispensed by moving the plunger 11 and also the rod 12 forwardly, which movement of the rod is permitted by the washer 73. Once a connected cartridge is empty, the entire mechanism cannot be re-used since the rod cannot be moved back to its initial position and so the mechanism is scrapped.

The modified end cap 14A has axially-projecting resilient fins 77 which engage internal ribs within the plunger 11, but when the plunger can no longer rotate, the fins 77 will ride over the ribs should cap rotation be continued. The cap itself is held on the plunger by an integral key received in a peripheral groove 11A adjacent the rear end of the plunger 11 (FIG. 9).

FIGS. 10 and 10A show a modified form of the second embodiment, differing in that the one-way clutch mechanism 18 is of the same form as that of the first embodiment, and so having two balls 22 disposed in opposed channels 21 in the rod 12. This allows the use of a locking washer 78 having a pair of opposed teeth 79 fitting into the two channels respectively, of the rod. In other respects, the locking washer 78 operates in much the same manner as the locking washer 73 and will not be described further, here.

This modified second embodiment also includes a pre-setting facility. Some drugs may be prescribed according to body weight, age and so on, with the intention of a defined dose being given at regular times. For this purpose, the plunger 80 of this modified embodiment differs from plunger 11 and the rearward end of the injector is provided with a pre-set lock arrangement which permits the setting of a dose no greater than the pre-set amount. This pre-set lock arrangement includes a button 81 engageable with a rotatable ring 82 threadingly engaged with a pre-set stop 83, disposed around a central tubular portion 84 of the plunger 80. The end-cap 14 is also modified so as to include a central projection 85, rotatably connecting the cap to the central portion 84.

In use, pre-setting is performed by initially winding the end-cap 14 until the required dose is shown through window 42. The button 81 is then depressed which frees ring 82 for rotation; this is rotated until the pre-set stop 83 engages end-face 86 of the outer part 87 of the plunger 80, also carrying the dose numerals. The button 81 is then released so locking the ring 82. Thereafter, rearward movement of the plunger 80 is limited by the pre-set stop 83, to the maximum required dose and in the event that the end-cap 14 is further rotated, it will simply slip with respect to the plunger 80.

If the remaining dose in a cartridge is less than the pre-set dose, the plunger cannot be wound out to the pre-set dose by virtue of the inter-action of the arms 49 of the coupler 45 with the stop 17 on rod 12, as has been described above. The maximum available dose will then be displayed through the window 42.

The third embodiment, shown in FIGS. 11, 12, 13A and 13B, differs from the previous embodiments in that no plunger is provided for dispensing the dose. Instead of winding out the end-cap 14 and pressing the plunger home to deliver the medicament, the user rotates the end-cap until the desired dose appears in the window. After pushing the needle into the appropriate site, the user presses a side release button and the medicament is injected without further user participation, under the action of an internal spring. Apart from the changes required to the mechanism to give the above functionality, the mechanism is similar to the previous embodiments and insofar as is possible, like components are given like reference characters.

FIG. 12 shows the mechanism at its zero position and FIG. 11 when set to dispense a dose of medicament, immediately after release of the mechanism but before dispensing has commenced.

End-cap 90 is permanently snapped on to the rearward end of the tubular body 10. The end-cap has external splines 91 which engage with internal splines 92 on a track member 93 mounted both for rotation and axial movement within the tubular body 10. This track member defines a precision helix 94, corresponding to helix 37 on plunger 11, but here the helix is unbroken and the follower is in the form of a tooth 95 formed integrally with a side release button 97 pivoted to the body 10. The button is urged by an integral leaf spring 102 to the position shown in FIGS. 12 and 13B where the tooth is engaged with the helix. A spring 96 acting between the end-cap 90 and an internal shoulder in the track member 93 urges that track member to the left, the internal shoulder also engaging a coupler 45 having the same function as has been described above.

The side release button 97 co-operates with an interlock 98, to ensure the button 97 remains in its released position (FIGS. 11, 13A) once depressed, until an injection has been completed. The interlock 98 is urged rearwardly by a spring 100 within the button 97 acting on abutment 101 of the interlock, but is held against the action of that spring by the rearward edge of extension 103 of the interlock engaging the tooth 95, until the button is depressed. Then, the extension 103 of the interlock moves between the tooth 95 and the track member 93 under the action of spring 100, so preventing re-engagement of the tooth with the helix. On the track member being moved forwardly under the action of spring 96, the interlock is also moved forwardly by the track member, until the tooth 95 may once more drop into the track, moving the button outwardly under the action of spring 102, assisted by spring 100.

On turning the end-cap 90, the track member 93 is threaded rearwardly, until the required dose is visible through window 42. Then, on depressing the button 97, the tooth is released from the track, so permitting an injection to be given by the track member being thrust forwardly by spring 96.

In other respects, the mechanism is essentially similar to that of the previous embodiments; for example, it may be made as a re-usable device or as a disposable device. As the action is similar to that described above, it will not be described in further detail here.

What is claimed is:

1. An automatic one-way clutch mechanism for use in an incrementing mechanism having:
   a tubular body;
   a driving member rotatably and slidably mounted within the tubular body;
   an elongate element mounted within the tubular body and arranged to be advanced in one direction with respect to the tubular body upon operation of the driving member;
   which one-way clutch mechanism comprises:
   a channel extending along the elongate element;
   a generally conical surface formed internally on the driving member and surrounding the elongate element;
   a blocking clutch member located in the channel and engageable with the conical surface; and
   a freeing mechanism adapted to disengage the clutch by lifting the clutch member out af engagement with the conical surface so as to disconnect the driving member from said elongate element, which freeing mechanism comprises:
   a pressure component held against rotation with respect to the elongate element and arranged to engage the clutch member;
   a spring acting on said component to urge the component away from its clutch disengaging position; and
   two sets of inter-engageable teeth formed respectively around the driving member and around the pressure component;
   whereby rotation of the driving member with respect to the pressure component successively lifts said component against the action of the spring and then releases said component, the lifting serving to move the clutch member out of engagement with the conical surface and allows the spring to move the pressure component to a position where the clutch member engages said surface, through the interaction of the teeth riding over each other.

2. An automatic clutch mechanism as claimed in claim 1, wherein the generally conical surface is one of substantially continuous and wholly continuous.

3. An automatic clutch mechanism as claimed in claim 1, wherein the pressure component is additionally configured to urge the clutch member to its active, conical surface engaging position.

4. An automatic clutch mechanism as claimed in claim 3, wherein the teeth respectively around the driving member and around the pressure component do not fully inter-engage when meshed, whereby the pressure component still exerts force on the clutch member when the teeth are meshed.

5. An automatic clutch mechanism as claimed in claim 1, wherein there are two diametrically opposed similar clutch members, each acting between the conical surface and the elongate element.

6. An automatic clutch mechanism as claimed in claim 1, wherein the or each clutch member comprises one of a ball, a roller, and a wedging member.

7. An incrementing mechanism comprising a tubular body, a driving member slidably and rotatably mounted within the tubular body, an elongate element slidably mounted within the driving member and an automatic one-way clutch mechanism as claimed in claim 1 and arranged to effect coupling between the driving member and the elongate element when the driving member is moved in one direction with respect to the tubular body, and arranged not to drive the elongate element when the driving member is moved in the other direction with respect to the tubular body.

8. An injector device comprising a medicament-containing tube, a piston mounted within the tube, and an incrementing mechanism as claimed in claim 7 and arranged with the elongate member engaged with said piston, whereby incremental advancement of the elongate element effects dispensing of a dose of medicament by virtue of inter-action between the elongate element and the piston of the medicanient-containing tube.

9. An injector device as claimed in claim 8, wherein there is a further one-way clutch mechanism arranged between the tubular body and the elongate element, to resist movement of the elongate element in said other direction.

10. An injector device as claimed in claim 9, wherein the further one-way clutch mechanism is selectively releasable to permit resetting of the incrementing mechanism to an initial position.

11. An injector device as claimed in claim 10, wherein the selective releasing of the further one-way clutch mechanism is perfanned automatically by disconnecting said medicanient-containing tube from the injector mechanism.

12. An injector device as claimed in claim 8, wherein there is provided a non-resetrable ratchet arrangement between the tubular body and the elongate element, whereby the injector device must be disposed of following full movement of the elongate element in a dose-dispensing direction.

13. An injector device as claimed in claim 12, wherein the ratchet arrangement comprises a spring blade bearing on the elongate element and deflected in the direction of advancement of the elongate element.

14. An injector device as claimed in claim 8, wherein there is a dose pre-setting arrangement which permits the pre-setting of a maximum dose to be dispensed which maximum dose is less than the dose which otherwise could be delivered by the mechanism.

15. An injector device as claimed in claim 14, wherein the dose pre-setting arrangement includes a pre-setting ring, a pre-setting lock slidably mounted within the tubular body and with which the pre-setting ring is threadingly engaged, the driving member engaging the ring on being moved to pre-set the dose.

16. An injector device as claimed in claim 15, wherein a locking arrangement is provided for the pre-setting ring.

17. An injector device as claimed in claim 8, wherein there is provided a restrictor to restrict the setting movement of the driving member to a dose not greater than the remaining dose within the medicament-containing tube connected to the device.

18. An injector device as claimed in claim 17, wherein said restrictor includes an abutment engageable with a stop at or adjacent the elongate element remote from a connected syringe or cartridge which abutment is rotatably coupled to the driving member.

19. An injector device as claimed in claim 8, wherein the driving member is provided with an end-cap by means of which the driving member is turned to move the driving member in the other direction and by means of which the driving member is depressed in the one direction.

20. An injector device as claimed in claim 8, wherein the driving member is coupled to an end-cap to permit the rotation of the driving member thereby to move the driving member in the other direction, the driving member being spring-urged to move in the one direction and being provided with a releasable catch to hold the driving member against movement in the one direction, until released.

21. An injector device as claimed in claim 8, wherein the medicament-containing tube comprises one of a syringe to which the device is connected and a cartridge which is received within the injector device.

22. An injector device comprising:
   a medicament-containing tube;
   a piston mounted within the tube to eject medicament therefrom; and
   an incrementing mechanism for said piston,
said incrementing mechanism comprising:
   a tubular body;
   a driving member rotatably and slidably mounted within the tubular body;
   an elongate element mounted within the tubular body and arranged to be advanced in one direction with respect to the tubular body upon operation of the driving member, the elongate member engaging with said piston; and
   an automatic one-way clutch mechanism arranged to effect coupling between the driving member and the elongate element when the driving member is moved in one direction with respect to the tubular body and arranged not to drive the elongate element when the driving member is moved in the other direction with respect to the tubular body;
said automatic clutch mechanism comprising:
   a channel extending along the elongate element;
   a generally conical surface formed internally on the driving member and surrounding the elongated element;
   a blocking clutch member located in the channel and engageable with the conical surface; and
   a freeing mechanism adapted to disengage the clutch by lifting the clutch member out of engagement with the conical surface so as to disconnect the driving member from said elongate element;
said freeing mechanism comprising:
   a pressure component held against rotation with respect to the elongate element and arranged to engage the clutch member;
   a spring acting on said component to urge the component away from its clutch disengaging position; and
   two sets of inter-engageable teeth formed respectively around the driving member and around the pressure component;
whereby rotation of the driving member with respect to the pressure component successively lifts said component against the action of the spring and then releases said component, the lifting serving to move the clutch member out of engagement with the conical surface and allows the spring to move the pressure component to a position where the clutch member engages said surface, through the inter-action of the teeth riding over each other.

* * * * *

UNITED STATES PATENT AND TRADEMARK OFFICE
CERTIFICATE OF CORRECTION

PATENT NO. : 6,899,698 B2
DATED : May 31, 2005
INVENTOR(S) : Bernard Sams

It is certified that error appears in the above-identified patent and that said Letters Patent is hereby corrected as shown below:

Column 10,
Line 32, reads "lifting the clutch member out of engagement with the" should read
-- lifting the clutch member out of engagement with the--

Column 11,
Line 20, reads "the medicanlent-containing tube." should read
-- the medicament-containing tube. --
Line 31, reads "is perfanned automatically by disconnecting said"
should read -- is preformed automatically by disconnecting said --
Line 34, reads "there is provided a non-resetrable ratchet arrangement" should read
-- there is provided a non-resettable ratchet arrangement --

Column 12,
Line 41, reads "driving member and surrounding the elongated" should read
-- driving member and surrounding the elongate --

Signed and Sealed this

Twelfth Day of July, 2005

JON W. DUDAS
*Director of the United States Patent and Trademark Office*